(12) United States Patent
Rose et al.

(10) Patent No.: US 9,995,621 B2
(45) Date of Patent: Jun. 12, 2018

(54) SOUND SENSOR

(71) Applicant: Sophie Elizabeth Clarke, Ferndown (GB)

(72) Inventors: Darren Rose, Wimborne (GB); Roger Hurrey

( * ) Notice: Subject to any disclaimer, the term of this patent is extended or adjusted under 35 U.S.C. 154(b) by 98 days.

(21) Appl. No.: 14/771,059

(22) PCT Filed: Feb. 14, 2014

(86) PCT No.: PCT/GB2014/000051
§ 371 (c)(1),
(2) Date: Aug. 27, 2015

(87) PCT Pub. No.: WO2014/125242
PCT Pub. Date: Aug. 21, 2014

(65) Prior Publication Data
US 2015/0377693 A1 Dec. 31, 2015

(30) Foreign Application Priority Data
Feb. 14, 2013 (GB) .................. 1302575.4

(51) Int. Cl.
*G01H 11/06* (2006.01)
*G01N 29/30* (2006.01)
*G01H 11/08* (2006.01)
*G01H 1/00* (2006.01)
*G01N 29/24* (2006.01)
*G01N 29/14* (2006.01)
*G01H 3/12* (2006.01)
*H04R 17/02* (2006.01)

(52) U.S. Cl.
CPC ............ *G01H 11/06* (2013.01); *G01H 1/003* (2013.01); *G01N 29/14* (2013.01); *G01N 29/2437* (2013.01); *G01H 3/12* (2013.01); *G01H 11/08* (2013.01); *H04R 17/025* (2013.01)

(58) Field of Classification Search
CPC .......... G01H 11/08; G01H 11/06; G01H 3/12; G01H 1/003; G01N 29/14; G01N 29/2437; G01M 3/24; G01M 3/243
See application file for complete search history.

(56) References Cited

U.S. PATENT DOCUMENTS

| 4,068,209 | A | * | 1/1978 | Lagier | ................. | B06B 1/0618 |
| | | | | | | 367/158 |
| 4,461,177 | A | * | 7/1984 | Feng | ................... | B06B 1/0677 |
| | | | | | | 73/587 |
| 4,796,725 | A | * | 1/1989 | Katayama | ............. | H04R 19/00 |
| | | | | | | 181/142 |
| 5,872,307 | A | * | 2/1999 | Brammer | ............. | G01L 23/222 |
| | | | | | | 73/35.11 |

(Continued)

FOREIGN PATENT DOCUMENTS

| DE | 2459729 | * | 6/1976 |
| EP | 0679874 | * | 11/1995 |

*Primary Examiner* — Helen Kwok
(74) *Attorney, Agent, or Firm* — William H. Bollman

(57) ABSTRACT

A compression assembly (5) forms an airborne sound sensor for detecting sound pressure level. The airborne sound sensor includes a piezo electric transducer (11) compressed against a top element (9) and a lower element (12) so as to compress the transducer (11) across a first face and a distal second sensing face.

19 Claims, 2 Drawing Sheets

(56) References Cited

U.S. PATENT DOCUMENTS

| | | | | |
|---|---|---|---|---|
| 6,127,770 A | * | 10/2000 | Hauser | G01H 1/00 |
| | | | | 310/324 |
| 2004/0050163 A1 | * | 3/2004 | Komninos | G01N 29/14 |
| | | | | 73/587 |
| 2010/0005954 A1 | * | 1/2010 | Higashidate | G10H 3/143 |
| | | | | 84/725 |

* cited by examiner

SOUND SENSOR

FIELD OF THE INVENTION

The present invention relates generally to an airborne sound sensor in the form of a compression assembly for detecting airborne sound. The system reduces the risk that workers will be exposed to dangerous high pressure gas jets which the industrial workers cannot see or hear escaping from high pressure industrial pressurized gas systems.

BACKGROUND

In many industrial environments the use of pressurised piping is commonplace, such as oil rigs, refineries, gas production and storage facilities and power generation plants which usually contain complex pipe networks to move a variety of hazardous and non-hazardous high pressure media such as gas and liquids. The pipes can also be used for operating or controlling processes as well as distribution of process and end gas product. The gas can potentially be toxic or explosive which may require immediate action although any pressurised gas leak should be dealt with in the utmost of urgency and therefore requires careful monitoring of leaks.

Other industrial operations which produce pressurised gas or which rely on pressurised gas as part of machine operation contain mechanical parts which may produce ultrasound when components wear or are under stress.

Historical ultrasonic noise evaluation of most industrial sites indicates that most man-made noise occurs in the acoustic range whereas a pressurised gas leak produces a broadband sound pressure level that spans the acoustic and ultrasonic range. The size of the ultrasonic sound signal is a function of many variables which include the upstream to downstream pressure differential, leak size, gas type and gas temperature and type of pressurised system, driven or closed. It is important to establish whether a system is driven using a pressure generator, such as a pump, to maintain system pressure, or if the system is closed, such as a pressure vessel, to establish the potential leak profile intensity and duration. If the system is driven by a constant pressure the leak profile will remain reasonably constant for the leak duration with minor fluctuations across the frequency range whereas a closed system will experience rapid cooling due to energy transfer and the sound pressure level will diminish rapidly across the frequency range with minor fluctuations which requires instantaneous detection to avoid gas pools going undetected. It should be noted that although no two gas leaks will produce an identical profile the broadband characteristic which decreases in intensity with increasing frequency allows the leaks to be susceptible to detection.

PRIOR ART

Ultrasonic gas leak detectors are already available and typically operate in the ultrasonic frequency range of 25 kHz to 100 kHz to eliminate man-made acoustic noise and avoid false alarms. The detectors are typically mounted on a pole or in a position above sensing area (for example on a pole or wall about 3 m height) in order to increase the sensing range which is typically hemi-spherical or cone shaped.

To avoid further false alarms the detectors are set up on an installation-by-installation basis with the alarm level set to a point above peak ultrasonic background level (typically peak background +6 dB for backgrounds below 74 dB) and then monitored during full process before they are used for alarm purposes. An additional measure for non-toxic applications can be to apply a delay time to the alarm function to eliminate short-term ultrasonic sound spikes produced by metal tags, pressure release valves and other maintenance activities such as hammering, sand blasting and pressure washing.

Existing detectors are supplied with a relatively large dynamic range compared to the area of interest as they are required to cover all areas of industrial environments from 44 to +104 dB with one standard detector which leads to decreased sensitivity of the output signal.

A further requirement is to ensure a satisfactory Safety Integrity Level (SIL—EN61508 for example) to maintain functionality. This is currently done in one of two ways, through detector design and component evaluation in simple detectors or with detector design and component evaluation coupled with a means of self-test in complex detectors.

Examples of the first way using detector design and component evaluation are typically found in low power Intrinsically Safe detectors whilst examples of the second way include background monitoring where the ultrasonic background level exceeds the lower end of the detector dynamic range causing an elevated signal level, an externally mounted piezoelectric transducer as described in EP 1522839, an internal pressurised air jet as described in US 2011120209 and an electronic test that pulses the detector components with a known voltage.

The first type of SIL using detector design and component evaluation has a disadvantage in the fact that there is no positive feedback to the control room to indicate that the detector is still functional so maintenance needs to be undertaken on a regular basis and due to the height of the detectors this usually incurs cost. This type of detector typically achieves a low rating level of SIL1/2 which can exclude use on some safety critical systems.

The second type using background levels do not work when the background noise level is below the detector dynamic range. If background levels are in the detector dynamic range the lack of detector sensitivity usually requires further verification to produce a signal that can be accurately measured especially on older installations, both instances would require regular cost y maintenance. This type of detector would also typically achieve a low rating level of SIL1/2.

Disadvantages of the externally mounted piezoelectric transducer as described in EP 1522839 are described in US 2011120209. To produce a noise capable of fully testing the sensor the test duration is typically in the region of 15 s at which point the detector is effectively deaf to the environment which may exclude use when toxic gas is present. The piezoelectric transducer also has a maximum output of approximately 100 dB which prevents use in areas with high background noise. This type of detector typically achieves a rating level of SIL2/3 but would have restrictions on installation environments.

Disadvantages of the internal pressurised air jet as described in US 2011120209 are in the number of moving parts and the possibility of nozzles or tubing to become blocked, especially in harsh environments. This type of test also suffers from the drawbacks mentioned for the piezoelectric transducer but also due to the complexity of the air pressure jet components this type of detector typically achieve a low rating level of SIL1/2 whilst also requiring restrictions on installation environments.

Further disadvantage for the methods described in EP 1522839 and US 2011120209 are found in the power required for operation which excludes use in Zone 0 (A place in which an explosive atmosphere—consisting of a mixture with air of dangerous substances in the form of gas, vapour o mist—is present continuously or for long periods) environments.

The disadvantage with an electronic test using a voltage pulse are only the internal components are tested meaning that if sensor and sensor/ingress protection screen becomes detached the test will still indicate a pass condition even though the detector has effectively become deaf due to the air pocket produced by the detachment. The sensor and sensor/ingress protection screen in a 'floating crystal' type detector is only attached using the adhesive qualities of the epoxy sealant and may become detached due to vibration, aging or attack from chemicals. The sensor could also be damaged, if the sensor cracks due to impact it would result in a loss of sensitivity whilst still achieving a test pass condition, this type of detector typically achieves a rating level of SIL2.

So existing forms of SIL detection have reliability problems, do not possess adequate rigour and have exclusions on installation environments.

Other acoustic sensors have been developed for various applications, mostly unrelated to detecting leaks from high pressure piping, and so are unsuitable for this use. A few examples are note below.

German Patent Application DE-A1-3023155 (Telemit Electronic GmbH) teaches use of a piezoelectric contact microphone with a stressed piezo-pillar. Electrical connection is from a plate (3) at the base of the piezo-element (2) and a second contact (6) at the base of the housing. The microphone is for speech reproduction with low susceptibility to interfering background noise.

European Patent Application EP-A2-0679874 (Siemens AG) teaches a sound sensor having a piezoelectric oscillator in contact with an electrically conductive housing on one side and a contact foil on the opposite side. A pressure element presses the piezoelectric oscillator against the housing base via the contact foil.

UK Patent Application GB1529468 (Thompson-CSF) teaches an underwater electroacoustic sensor operable at great depth. This sensor is not suitable for detecting airborne sound. It comprises a piezoelectric ceramic held between a relatively massive front plate and a counter mass.

Japanese Patent Application JP-S-A-5639699 (Tokyo Shibaura Electric Co) teaches an acoustic sensor having a piezoelectric element within a rigid housing, compressed against the base of the housing by a spring. Between the spring and the piezoelectric element is a relatively massive bumper and electrode plate. The coil spring is selected according to inductance.

U.S. Pat. No. 4,461,177 (Dunegan Corporation) relates to an acoustic emission sensor, which is used to listen to sounds generated with a monitored object cracks. This sensor is adapted to detect sounds emitted from solid objects and is not suitable as a sensor to detect airborne vibrations. It comprises acoustic elements compressed between a front mass and a counter mass by a nut and bolt. The piezocrystal is enclosed within, a rigid and relatively massive housing.

US Patent Application US-A1-2010/0005954 (Higashidate et al) describes a sound detector which can be used to detect sounds generated by a musical instrument. A magneto strictive material is compressed between two bias magnets.

All including Telmit, Siemens, Thompson-CSF, Tokyo Shibaura Electric, Dunegan Corporation teach piezo crystal with massive bases and/or bumpers blocking sensor faces of the crystal enclosed within a rigid and relatively massive housing which covers the sensing face of the transducer.

Both Telmit and Siemens reveal sensors requiring an electrically conductive housing.

EP-A2-2442124 (Eaton Corporation) teaches an acoustic sensor for detecting electrical conductivity faults. This sensor comprises a piezoelectric element. An optional preload, which is not required, compresses the piezoelectric element. The sensor is fastened to an electrical power conductor. This sensor is not suitable for detecting airborne sound.

U.S. Pat. No. 5,872,307 (Robert Bosch GmbH) describes a knock sensor, which detects knocking sounds/vibrations generated by an engine. This sensor comprises a piezo ceramic disc compressed between a seismic mass and housing by a plate spring International Patent Application WO9726513A1 (Forschungszentrum Karlsruhe GmbH) relates to an acoustic sensor, for use in laser induced photo acoustic spectroscopy. A piezo element is compressed between an insulation plate and a pressure pad by a spring which acts against a housing member via a spacer. A diaphragm covers the pressure pad 8.

SUMMARY OF THE INVENTION

According to a first aspect of the invention, there is provide a compression assembly for detecting sound pressure level, comprising: a transducer arranged to convert airborne sound to an electrical signal, having a detection side sensing face and a distal non-detection side face, an electrode, and a detection side element and a non-detection side element compressing the transducer across the faces thereby pressing a first portion of the electrode into electrical contact with the detection side sensing face; characterized in that the non-detection side element comprises a first conductive pathway in contact with the non-detection side face, and a second conductive pathway in electrical contact with a second portion of the electrode.

Thus there is a compression assembly for detecting sound pressure level using a transducer compressed against a top element and a lower element so as to compress the transducer across the sensing faces.

Preferably there is a compression assembly for use with an acoustic sensor using a transducer having both a detection side compressed against a top element and a non-detection side compressed against a lower element so as to compress the transducer between the top element and the lower element.

Preferably the compression assembly comprises a resilient means arranged to urge the lower element against the transducer and thereby urge the transducer against the top element. Advantageously the resilient means deforms and therefore there is no need for critical manufacturing tolerances to maintain the desired compression pressure because the resilient means deforms as required.

Preferably the resilient means is squeezed between the lower element and a reaction structure immovable with respect to a connection to the top element. The reaction structure is a member that is relatively stiff and practically undeformable compared to the resilient means. Preferably the reaction structure is immovable with respect to the detection side element which braces the resilient means. Therefore the reaction structure acts similar to a stiff portion of a clamp. The compression assembly is compressed with the aid of the reaction structure. The compression assembly being effectively clamped by the reaction structure with the aid of the resilient means to maintain a desired compression pressure between the detection side and the top element and also between the non-detection side and the lower element.

Preferably the reaction structure is fixed to the detection side element.

Preferably the reaction structure comprises an end-stop arranged to limit the distance that the lower element can travel in a direction pointed from the detection side to the non-detection side. Advantageously the end stop stops a hard knock to the acoustic sensor causing resilient means to be deformed to the extent that damage could occur to the compression assembly.

Preferably the lower element comprises a first conductive pathway pressed into electrical contact with the non-detection side. Advantageously the compression afforded by the compression assembly establishes a reliable electrical connection to the transducer.

Preferably there is an electrode compressed by the top element into electrical contact with the detection side. Advantageously the compression afforded by the compression assembly establishes a reliable electrical connection to the transducer.

Preferably the lower element comprises a second conductive pathway in electrical contact with an electrode. Advantageously the lower element comprises a printed circuit board comprising the first conductive pathway. So a simple and inexpensive easily mass produced lower element is utilized incorporating the first conductive pathway and also preferably the second conductive pathway.

The printed circuit board is typically a fiberglass or polyester panel and is less dense and less massive than the transducer which is typically a piezo-electric crystal. Thus the compression assembly comprises a relatively dense and massive transducer compressed between a relatively less dense and less massive detection side element and non detection side elements where these side elements are preferably panels, typically made from fiberglass or polyester. Advantageously a cover seal is formed where the detection side is compressed against the top element. Preferably the seal is capable of preventing seepage of liquids or gases which could harm the transducer or any of the aforementioned electrical components and connections.

Preferably the top element comprises a central aperture surrounded by the cover seal. Advantageously the aperture allows sound and vibration to reach the detection side unoccluded by the portion to the top element that would otherwise occlude the detection side from sound and vibration that stimulates the acoustic sensor.

Preferably the top element comprises a caulking compound closing the central aperture. Preferably the caulking compound is waterproof. Advantageously the caulking compound causes negligible attenuation of the sound and vibration passing through the aperture.

Advantageously the detection side is sensitive to sound and vibration.

Preferably the transducer produces a voltage difference between the detection side and the non-detection side as a result of sound or vibration that impinges upon the detection side. Advantageously a piezoelectric crystal will operate as the transducer.

Preferably the transducer has a cylindrical form between the detection side and the non-detection side. Preferably the transducer is a right circular cylinder, the faces of which are the detection side and the non-detection side.

Preferably the compression assembly is mounted to the acoustic sensor so that the top element is arranged to transmit sound and vibration unoccluded by the cover seal.

According to the second aspect of the invention there is an acoustic sensor comprising a self-test module arranged to provide an electrical excitation between the first conductive pathway and the second conductive pathway where said electrical excitation is formed to cause a resonance frequency of the compression assembly to be excited. The resulting strength of the resonance of the assembly and its exact centre frequency can then be measured to determine correct functionality of the compression assembly and detection circuitry.

Preferably the resonance frequency of the compression assembly is below the resonance frequency of the transducer.

Advantageously the resulting resonance signal strength will be many times higher than signal strength expected during normal detector operation so functionality can be determined for any background level.

Advantageously the strength of the resonance signal can be easily established in milliseconds to allow continuous determination of functionality as part of the sensor detection cycle resulting in increased detector performance.

Advantageously improper operation due to both physical or electrical fault will be detected. For example if the transducer is cracked due to impact or shock or if delamination occurs between sound sensitive surfaces the preselected voltage will cause the assembly to resonate differently from the case where there is no fault.

According to a third aspect of the invention there is a method for increasing the output signal sensitivity of the sensor in response to a stimulus of sound and/or vibration. The minimum background noise level should be determined and the minimum signal output should be set to a level equal to or just below the determined value, the maximum signal output should then be set to a value above the determined level. The maximum signal output value would typically be the equivalent of background +6 dB although this level may be increased or decreased depending upon application of the sensor.

Advantageously the signal output can be adjusted in multiple steps to suit any installation, with signal output range either representing full sensor dynamic range, as per existing detectors, or representing only a part of the sensor dynamic range, with the signal output range representing any value from one dB or less sensor output range, up to the full sensor dynamic range, and with the starting point in the sensor dynamic range adjustable to any value in that range, in steps, for example one dB steps.

The invention will now be described, by way of example only, with reference to the accompanying drawings in which:

BRIEF DESCRIPTION OF THE FIGURES

The following figures provide a better understanding of the present invention by way of example only.

DETAILED DESCRIPTION OF PREFERRED EMBODIMENTS OF THE INVENTION

Figure 1:
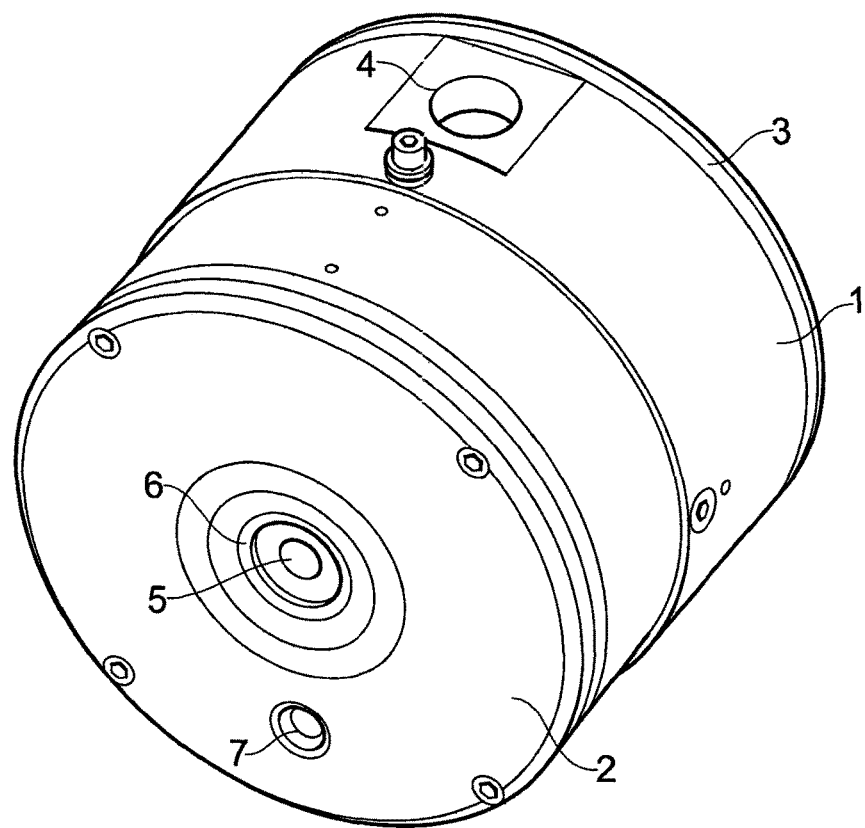
FIG. 1 is a perspective view of the gas leak detector showing the sensor compression assembly.

Referring to FIG. 1 an ultrasonic gas leak detector comprises a housing 1 which is machined or fabricated from any material applicable to the installation environment and/or certification requirements. The detector has overall dimensions of 105 mm high by 125 mm in diameter and weighs about 1.5 kg if the housing is made from aluminum or about 4 kg if the housing is made of stainless steel. As such the detector is not intended to be hand-held although the compression assembly 5 for an acoustic detector? shown in FIG. 2 could be used in a portable device if required. The detector shown in FIG. 1 comprises an electronics enclosure 1, front cover 2 and terminal cover 3 which houses the compression assembly 5, electrical and electronic components. The detector has a cable entry 4 for power and signal and a visual indicator 7 to show correct functionality and fault condition. Compression assembly 5 is a faraday cage to isolate the sensor from external electrical interference and therefore the detector front cover 2 needs to be electrically insulated from the compression assembly 5. This is achieved by using an insulated spacer 6 made from any non-electrically conducting material.

Figure 2:
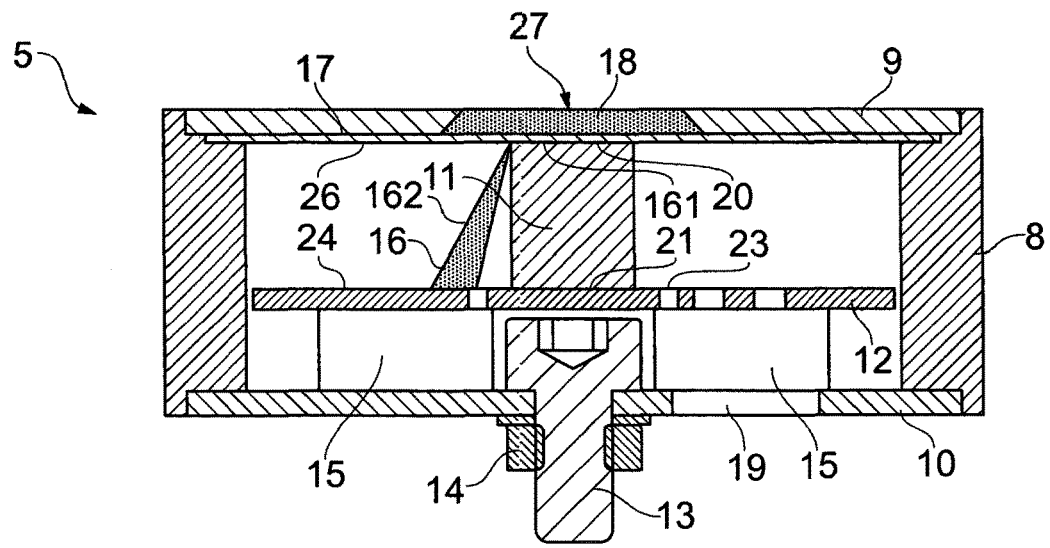
FIG. 2 shows a cross section of the sensor compression assembly

Referring to FIG. 2 the sensor assembly is a compression assembly 5 consisting of a piezoelectric transducer 11 with a natural frequency range outside of the detector operating frequency to eliminate natural resonance in the dynamic range of the detector. Selecting a piezoelectric transducer that is appropriate has been well documented and a good example can be found in US 2011120209. Unlike the piezoelectric transducer referenced in US 2011120209 the transducer assembly in FIG. 2 is connected at both faces.

The piezo transducer 11 has the shape of a column. Preferable geometries of the piezo transducer 11 shape are: a solid round cylinder with flat parallel ends, a solid square or rectangular cylinder block with flat parallel ends, or another column shape with flat parallel ends. The piezo transducer has a diameter if the shape is that of a round cylinder. It has a width if the shape is that of a square, rectangle, or other multisided outline. The flat parallel ends are referred to as the non detection side and the detection side. The face on the non detection side is the non detection side face. The face on the detection side is the detection side sensing face.

The non detection side sensing face on the non detection side flat parallel side of the piezo transducer 11 is attached directly to a first side of the piezo PCB 12 lower element (non-detection side element) using conductive adhesive, preferably conductive epoxy. This first end of the piezo transducer 11 is the non-detection side of the piezo transducer 11. PCB 12 could also be made from another material, either rigid or flexible provided it can maintain the piezo transducer in compression. Conductive tracks in the piezo PCB 12 lead from the piezo transducer 11 to a cable connector thereby electrically connecting the piezo transducer and the cable connector.

An electrode 16 is electrically bonded to the PCB 12 and the piezo transducer 11 to the surface on the detection side. Specifically the second portion of the electrode 162 is bonded to the second conductive pathway 24 in the PCB 12.

As shown in FIG. 2 the detection side element 9 has a central region comprising a sheet-like portion 26 pressing against the first portion of the electrode 161 and thereby applying pressure against the detection side sensing face of the transducer 11. The sheet-like portion may be in the form of a thin rigid panel such as a thin printed circuit board type panel, or the sheet like portion may be in the form of a flexible membrane. The non detection side element is a thin rigid panel such as a printed circuit board.

An advantage of the side elements being thin panels or membranes is that they are relatively less massive and dense compared to the transducer which aids the natural frequency of the transducer to be higher than that of the compression assembly. It also simplifies the assembly to a transducer between two relatively simple elements. This is a low cost construction. The side elements do not corrode or carry electricity except in the region of the printed circuit board where there are on surface and/or embedded conductive paths.

The detection side element 9 comprises peripheral region, surrounding a hole 27 in the central region having a larger diameter or width than the sensing face of the transducer, to which the sheet-like portion 26 is attached so as to cover the hole in the central region. As shown in FIG. 2 the peripheral region is in the form of a flat outer ring which is an inexpensive and simple form. The outermost edge of the peripheral need not be circular, nor is it necessary for the perimeter of the hole to be circular. An advantage of the hole is that the sound and vibration to be detected passes though the hole to impinge upon the sensing face 20 of the transducer 11. Thus the detection side element 9 does not obscure or occlude the sensing side face from the airborne sound and vibration that is to be detected.

The environmental seal 18 is cover seal 18 that occupies the hole in the central region so to cover the sheet-like portion 26. The cover seal 18 a waterproof compound and has relatively low mass and low density compared to the transducer 11.

Ideally the sheet-like portion 26 is stretched across the hole in the central region. An advantage is that the sheet like portion covers the sensing face 20 and presses the electrode 16, 161 against the sensing face. Ideally the electrode is a thin metal foil, or at least the first portion of the electrode 16 is a metal foil sandwiched between the membrane and the detection side sensing face. An advantage is that the total thickness of the sheet-like portion plus the thin foil electrode is minimal presents minimal attenuation to the sound and vibration before reaching the sensing face. Referring to FIG. 1 there is a front cover 2 supporting a portion of the detection side element 9 having a central opening exposing the detection side element 9 to airborne sound.

Figure 3:
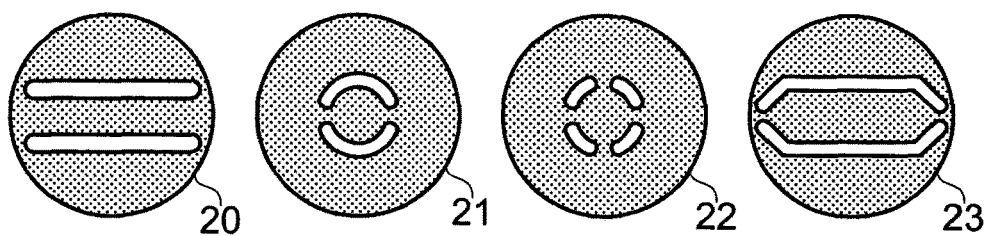
FIG. 3 shows examples of compression plates.

It is important that the compression assembly containing 11, 12 and 16 has a natural resonant frequency outside of the detector frequency range and the natural resonance of the piezo transducer 11. In this embodiment this is achieved by selecting a piezo transducer with a high frequency resonance as previously stated so it is important to eliminate high frequency resonance from the remaining assembly components. FIG. 3 shows examples of 12 with material removed around the piezo transducer contact area to eliminate high frequency resonance using damping.

To eliminate spurious electrical noise acting on the piezo transducer 11 the assembly is then housed in a faraday cage made of electrically conductive material items 8, 9 and 10. The top cover 9 (detection side element) has a through hole which is of a larger diameter or width than the piezoelectric transducer 11 so that sound waves are not obstructed and also in this instance contains a bevel that acts as a mechanical retainer for the environmental seal 18. It is important that the material used for the environmental seal does not flood the inside of the faraday cage so a double sided adhesive material 17 is used on the inside of detection side element 9 to act as a seal. The piezo transducer 11, PCB 12 and electrode 16 are then attached to the inside of the adhesive material 17. The environmental seal 18 is then applied or attached to protect the assembly from ingress of moisture, particles, or any other airborne contaminants. The seal 18 is usually in the form of a liquid or paste which sets to solid such as epoxy or liquid rubber and must be left to set prior to further assembly.

To ensure that the assembly is under compression, springs 15 are inserted underneath the piezo PCB 12, which is the non detection side element 12, prior to assembly of the non detection side cover 10 (reaction structure). The compression springs may take the form of a coil spring, rubber material block or disk, or other such resilient member which will act as a compression retainer. The compression spring(s) reacts against the non detection side cover 10 and the piezo PCB 12 that is the non-detection side element, thereby compressing the piezoelectric transducer 11 along its column length.

To ensure the spring assembly does not experience excessive movement and the transducer becoming detached from environmental seal 18 an end stop 13 is fitted to the non detection side cover 10 and retained using a locknut 14. The end stop 13 should allow between 0.25 and 0.5 mm movement. Therefore the compression spring compresses up to between 0.25 and 0.5 mm, the piezo PCB 12 moves up to a maximum of this distance range. The end stop 13 is arranged to limit the distance that the transducer can travel in the direction of the non-detection side by blocking the non detection side element.

The non detection side cover 10 has a cable through hole 19 and the cable wires pass through this. The cable wires carry sensor signals and if required test signals to and away from the piezo PCB, that is the non detection side element 12. The cable wire is connected to the piezo PCB connection.

A self-test module, not shown, is electrically connected to first and second conductive pathways in the non detection side element. The first conductive pathway 23 is pressed electrically into contact with the non detection side face of the transducer 11 and the second conductive pathway is electrically connected to the electrode 16 connected to the detection side sensing face 20 of the transducer. Thereby the self test module is arranged to provide an electrical signal corresponding to the resonance frequency of the compression assembly 5 and detect a signal corresponding to the resonance frequency of the assembly.

The cable wires carry signals generated by the piezo transducer to a main electronic circuit in the detector enclosure 1.

Whilst the preferred sensor is a piezoelectric transducer, other transducers that can sense sound pressure whilst under compression may also be used. Most off-the-shelf microphones do not contain a sensor that meets this requirement.

Control systems used for detector alarms may have been in use for many decades and the cost of upgrading the systems for use with modern detectors can be prohibitive. Older systems may only be accurate to several milliamps so detector output must be scaled to increase control system accuracy.

Figure 4:
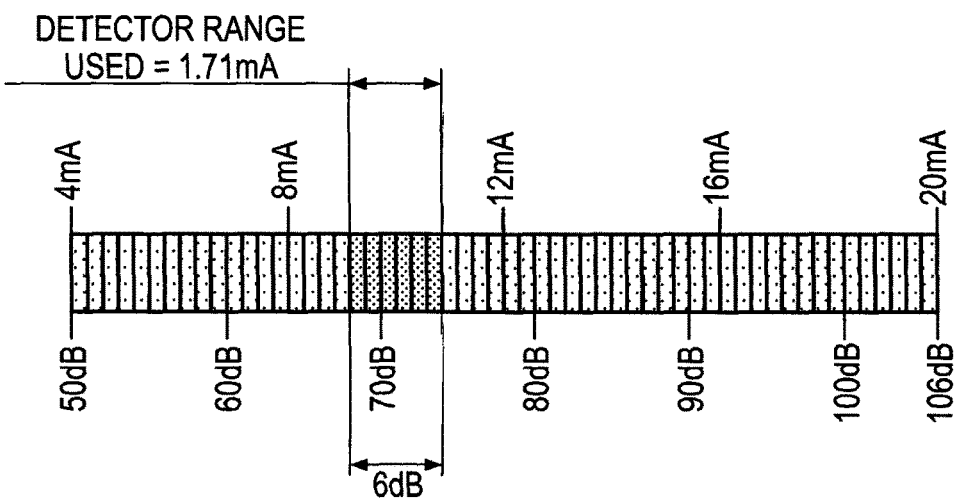
FIG. 4 is a graph showing extent of signal use for gas leak detection with a large dynamic range.
Figure 5:
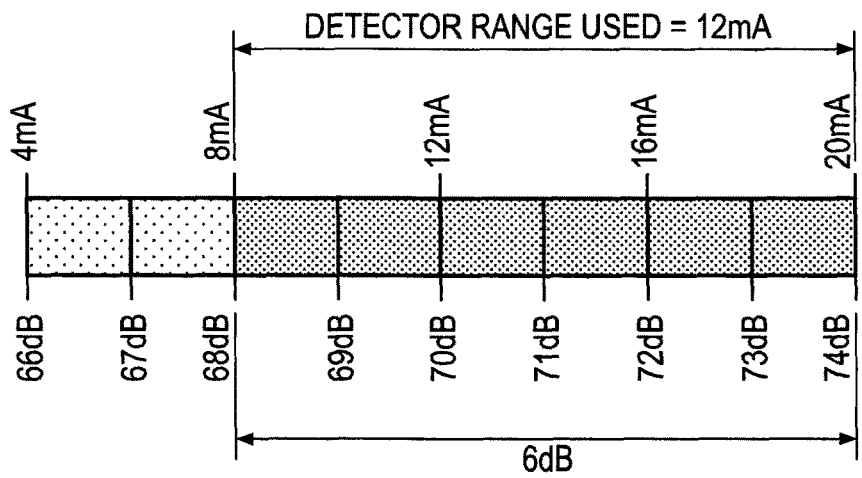
FIG. 5 is a graph showing the extent of signal use for gas leak detection with an active dynamic range.

Referring to FIG. 4 a scale is shown for a detector with a fixed 4-20 mA output and dynamic range of 50 to 106 dB to highlight the lack of sensitivity in current forms of detection. The detector is set up for use in an installation with a 68 dB background level, the alarm would typically be set at background level plus 6 dB (74 dB) which is shown in the dark shaded area. This would result in 1.71 mA of the detectors working range or 0.285 mA per 1 dB which may go undetected by older control systems. Using amplifiers in the detector to adjust the dynamic range of the detector signal output, the percentage of the detector dynamic range used is reduced, and therefore the sensitivity at the output is increased. FIG. 5 shows a detector with the dynamic range trimmed to work between 66 and 74 dB, the lower dB level is set below the background noise level (68 dB) to allow for background monitoring but this could be increased or decreased as appropriate. Using the trimmed dynamic range the detector now has a signal output of 2 mA per 1 dB which will allow use with older control systems and increase signal sensitivity on newer control systems.

An improvement to existing piezoelectric self-test methods is to add an additional electrical signal test to a voltage pulse test, if any, to test the self-resonance of the compression assembly. A piezoelectric transducer will respond to an electrical charge, as in existing methods, but this will not entirely check the integrity of the sensor structure if the transducer or compression assembly is damaged. To overcome the shortfalls it is recommended to apply to the piezoelectric transducer either a narrow pulse or a controlled frequency electrical signal. For a typical piezoelectric transducer the controlled frequency should be at or near its self-resonant frequency, typically a higher frequency than the ultrasonic frequency sensing range of the detector. This will ensure that the sensor is still within the defined detector limit as the self-resonance parameters are critical to the detector response to sound pressure level. In particular the amplitude and exact frequency of the resulting resonance will change if the assembly is disturbed and the transducer becomes wholly or partially separated from the protective screen, or if the transducer is damaged. The detector measures the amplitude and optionally exact frequency of the resulting resonance, and compares them with the factory values. The frequency pulse can be supplied to either face of the piezoelectric transducer at intervals that are appropriate to the safety integrity levels required by the detector.

Whilst the preferred sensor is a piezoelectric transducer, other transducers that can sense sound pressure and react to a resonant frequency may be used.

The piezoelectric transducer is sensitive to airborne sound and vibration of the audible and ultrasonic range.

In a minimal configuration the compression assembly comprises: a detection side element 9, an electrode 16, a transducer 11 having a sensing face 20, and a non-detection side element 12, wherein the detection side element 10 presses the electrode 16 against the sensing face 20, thereby compressing the transducer 11 against the non-detection side element 12. Thus the transducer is compressed between the detection side element 10 and the non detection side element 12.

As shown in FIG. 2, the detection side element 9 is in the form of a thin flexible membrane or sheet where the detection side element covers the sensing face 20 of the transducer 11. The thin sheet or membrane is located in the central region of the detection side element. The central region of the detection side element presses against the sensing face 20 of the transducer.

The invention has been described by way of examples only. Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the claims.

LIST OF ITEMS IN THE FIGURES

1 Enclosure
2 Front Cover

3 Terminal Cover
4 Cable Entry
5 Compression Assembly
6 Insulated Spacer
7 Visual Indicator
8 Tube
9 Detection Side Element
10 Non Detection Side Cover
11 Piezoelectric Crystal
12 Non Detection Side Element
13 End Stop
14 Lock Nut
15 Compression Spring
16 Electrode
161 First portion of electrode
162 Second portion of electrode
17 Seal (Adhesive Disc)
18 Environmental Seal
19 Cable Through Hole
20 Detection Side Sensing Face
21 Non Detection Side Face
23 First Conductive Pathway
24 Second Conductive Pathway
27 Hole in Detection Side Element

The invention claimed is:

1. A compression assembly (5) for detecting an airborne sound is mounted in a Faraday cage and comprises:
a piezo electric transducer (11) arranged to convert the airborne sound to an electrical signal, the transducer having a first sensing face (21) and a distal second sensing face (20);
wherein a nonconductive first element (12) and a second element (26) compress the transducer (11) across the first sensing face (21) and the distal second sensing face (20) with a desired pressure maintained by a reaction structure (8, 9, 10) which clamps the second element (26) to pressing a first portion (161) of an electrode (16) against and into electrical contact with the second sensing face (20) and which clamps the first element (12) to press a first conductive pathway (23) into contact with the first sensing face (21).

2. The assembly according to claim 1 comprising a resilient means (15) arranged to press against the first element (12).

3. The assembly according to claim 2 wherein the reaction structure (8, 9, 10) is immovable with respect to the first element (12) which braces the resilient means (15).

4. The assembly (5) according to claim 1 where the reaction structure (8, 9, 10) is fixed to the second element (26).

5. The assembly (5) according to claim 1 wherein the reaction structure comprises an end stop (13) arranged to limit a distance that the transducer (11) can travel in a direction from the second sensing face (20) toward the first sensing face (21) by blocking the first element (12).

6. The assembly (5) according to claim 1 wherein the first element (12) comprises a printed circuit board comprising the first conductive pathway (23).

7. The assembly (5) according to claim 1 wherein the second element (26) has less mass than the transducer (11).

8. The assembly (5) according to claim 1 wherein the second element (26) has a central region comprising a sheet-like portion pressing against the first portion (161) of the electrode (16).

9. The assembly (5) according to claim 8 wherein the reaction structure (9) comprises a peripheral region, surrounding a hole in the central region having a larger diameter or width than the second sensing face (20) of the transducer (11), to which the sheet-like portion (26) is attached so as to cover the hole (27) in the central region.

10. The assembly (5) according to claim 9 wherein the sheet-like portion (26) is stretched across the hole (27) in the central region.

11. The assembly (5) according to claim 9 wherein the peripheral region is in the form of a flat outer ring.

12. The assembly (5) according to claim 9 in which a cover seal (18) occupies the hole (27) in the central region so to cover the sheet-like portion (26).

13. The assembly (5) according to claim 12 wherein the cover seal (18) is a waterproof compound.

14. The assembly (5) according to claim 1 wherein the first portion of the electrode (161) is a metal foil sandwiched between the second element (26) and the second sensing face (20).

15. An ultrasonic airborne sound sensor for detecting gas leaks, comprising:
the assembly (5) according to claim 1; and
a front cover (2) supporting a portion of the second element (9) having a central opening exposing the second element (9) to the airborne sound;
characterized in that the front cover (2) is electrically insulated from the Faraday cage by an insulated spacer (6) made from a non-electrically conductive material.

16. The assembly according to claim 2 wherein the resilient means (15) is arranged to react against the reaction structure (8, 9, 10).

17. The assembly according to claim 1 wherein the first element (12) and the second element (26) are in the form of a panel or membrane.

18. The assembly (5) according to claim 1, wherein the first element (12) comprises a second conductive pathway (24) in contact with a second portion (162) of the electrode (16).

19. The assembly according to claim 1 wherein the reaction structure (8, 9, 10) forms the Faraday cage (8, 9, 10).

* * * * *